US006566549B1

(12) United States Patent
Greenblatt et al.

(10) Patent No.: US 6,566,549 B1
(45) Date of Patent: May 20, 2003

(54) CONTINUOUS POLYMERIZATION PROCESS AND PRODUCTS THEREFROM

(75) Inventors: Gary David Greenblatt, Rydal, PA (US); Barry Clifford Lange, Lansdale, PA (US); Michael Damian Bowe, Newtown, PA (US); Richard Foster Merritt, Fort Washington, PA (US); Robert Wilczynski, Yardley, PA (US); Gary Robert Larson, Hatfield, PA (US); Lori Marie Petrovich, Blue Bell, PA (US); David William Whitman, Sumneytown, PA (US)

(73) Assignee: Rohm and Haas Company, Philadelphia, PA (US)

( * ) Notice: Subject to any disclaimer, the term of this patent is extended or adjusted under 35 U.S.C. 154(b) by 288 days.

(21) Appl. No.: 09/212,038

(22) Filed: Dec. 15, 1998

Related U.S. Application Data

(63) Continuation-in-part of application No. 09/034,924, filed on Mar. 5, 1998, now abandoned, which is a continuation of application No. 08/467,685, filed on Jun. 5, 1995, now abandoned, which is a division of application No. 08/258,300, filed on Jun. 13, 1994, now abandoned, and a continuation-in-part of application No. 09/047,547, filed on Mar. 25, 1998.

(60) Provisional application No. 60/042,725, filed on Apr. 8, 1997, and provisional application No. 60/077,059, filed on Mar. 6, 1998.

(51) Int. Cl.$^7$ .............................. C08F 4/28; C08F 8/00; C08F 18/04; C08F 20/12; C08F 220/12

(52) U.S. Cl. .................. 560/202; 525/330.3; 525/330.6; 525/338; 525/62; 525/315; 525/361; 525/364; 525/378; 525/379; 525/390; 525/560; 525/561; 525/562; 526/88; 526/89; 526/207; 526/208; 526/209; 526/212; 526/216; 526/227; 526/318; 526/319; 526/324; 526/325; 526/328; 526/64

(58) Field of Search .......................... 560/202; 526/88, 526/227, 318, 64, 207–209, 212, 216, 319, 324–325, 328, 89; 525/330.3, 330.6, 338, 62; 524/315, 361, 364, 378–379, 390, 560–562

(56) References Cited

U.S. PATENT DOCUMENTS

| 4,158,736 A | 6/1979 | Lewis et al. ................. 560/205 |
| 4,356,288 A | 10/1982 | Lewis et al. |
| 4,529,787 A | 7/1985 | Schmidt et al. ............. 526/317 |
| 4,680,352 A | 7/1987 | Janowicz et al. |
| 4,694,054 A | 9/1987 | Janowicz |
| 4,914,167 A | 4/1990 | Hambrecht et al. |
| 5,268,437 A | 12/1993 | Holy et al. |
| 5,328,972 A | 7/1994 | Dada et al. |
| 5,576,386 A | 11/1996 | Kempter et al. |
| 5,710,227 A | 1/1998 | Freeman et al. |

FOREIGN PATENT DOCUMENTS

| DE | 4419 568 A1 | 6/1994 |
| EP | 0184761 B1 | 3/1990 |
| EP | 0 552876 A1 | 7/1993 |
| EP | 0590842 A2 | 4/1994 |
| JP | 53-91832 | 2/1980 |
| WO | WO 98/47927 | 10/1998 |

OTHER PUBLICATIONS

European Polymer Journal, vol. 8, pp. 321–328 (1972), Feit.
Chemical Engineering at Supercritical Conditions, pp. 515–533 (1983), Metzger.
Chemical Engineering, "Supercritical Fluid Conditions", edited by M. Paulaitis, J. M. L. Penninger, R. D. Gray, Jr. and P. Davidson, pp. 515–533. 1983.
European Polymer Journal, 1972, vol. 8, pp. 321–328, "Base–Catalysed Oligomerization of Vinyl Monomer—III", B. A. Feit.
Chemical Engineering News, "Regulation of Biotechnology Progresses", Jan. 7, 1985 pp. 27–28.

Primary Examiner—D. R. Wilson

(57) ABSTRACT

A continuous process for oligomers which do not contain, as polymerized units, carboxylic acid-containing monomers and their salts, including the steps of:

(1) forming a reaction mixture, substantially free of carboxylic acid-containing monomers and their salts, containing:
   (i) 0.5 to 99.95% by weight of the reaction mixture of at least one ethylenically unsaturated monomer; and
   (ii) 0.05 to 25% by weight, based on the weight of the ethylenically unsaturated monomer, of at least one free-radical initiator; and
(2) continuously passing the reaction mixture through a heated zone wherein the reaction mixture is maintained at a temperature of at least 150° C. and a pressure of at least 30 bars for from 0.1 seconds to 4 minutes to form terminally-unsaturated oligomers.

In addition, processes for forming oligomers of vinyl acetate and oligomers of vinyl alcohol are disclosed. Mixtures of fully saturated and terminally unsaturated oligomers are also disclosed.

17 Claims, No Drawings

CONTINUOUS POLYMERIZATION PROCESS AND PRODUCTS THEREFROM

This application is a continuation-in-part of U.S. application Ser. No. 09/034,924, filed Mar. 5, 1998, now abandoned, which is a continuation of U.S. application Ser. No. 08/467,685, filed Jun. 5, 1995, now abandoned, which is a divisional of U.S. application Ser. No. 08/258,300, filed Jun. 13, 1994, now abandoned; a continuation-in-part of U.S. application Ser. No. 09/047,547, filed Mar. 25, 1998, which claims the benefit of U.S. Provisional No. 60/042,725, filed Apr. 8, 1997; and claims the benefit of U.S. Provisional No. 60/077,059, filed Mar. 6, 1998.

This invention relates to a continuous polymerization process and products therefrom. In particular, this invention relates to a high temperature, high pressure, continuous polymerization process to produce oligomers. More particularly, this invention relates to a high temperature, high pressure, continuous polymerization process to produce terminally unsaturated and fully saturated oligomers. "Oligomers," as used herein and in the appended claims, refers to polymers having a degree of polymerization ("dP") of less than 50.

The art has long sought an inexpensive, efficient and environmentally sound way to produce low molecular weight polymers. However, production of these low molecular weight polymers has proven to be difficult.

One method of achieving low molecular weight polymers is through the use of efficient chain transfer agents, but this approach has several drawbacks. First, this approach incorporates the structure of the chain transfer agent into the polymer chain. This can be undesirable since that structure will have an increasing effect on the properties of the polymer as molecular weight decreases. Furthermore, the chain transfer agents commonly employed are mercaptans. These materials are expensive and have objectionable odors associated with their presence. Other common chain transfer agents are hypophosphites, bisulfites and alcohols. These also add to the cost of the process, impart functionality to the polymer, may introduce salts into the product, and may necessitate a product separation step.

Another way of lowering the molecular weight of the polymers is by increasing the amount of initiator. This approach adds considerably to the cost of production and may result in polymer chain degradation, crosslinking, and high levels of unreacted initiator remaining in the product. In addition, high levels of initiator may also result in high levels of salt by-products in the polymer mixture which are known to be detrimental to performance in many applications. The same is true for chain stopping agents, such as sodium metabisulfite. Among the preferred free-radical initiators for aqueous polymerization is hydrogen peroxide. It is relatively inexpensive, has low toxicity, and does not produce detrimental salt by-products. However, hydrogen peroxide does not generally decompose efficiently at conventional polymerization temperatures and large amounts must normally be used to generate enough radicals to carry out a polymerization.

High levels of metal ions, alone or together with high levels of initiator, have also been tried as a means for controlling molecular weight. Such an approach is unsuitable for some products that cannot tolerate metal ion contaminants in the polymer product, such as pharmaceutical, medical and electronic applications. In addition, depending on the metal ions used, the product may be discolored due to the presence of the metal ions.

U.S. Pat. Nos. 4,680,352 and 4,694,054 disclose processes for preparing low molecular weight terminally-unsaturated oligomers employing metal chelate chain transfer agents to control molecular weight. These processes suffer from the same problems as those processes employing high level of metal ions, as described above. In addition, because the methods employing the metal chelate chain transfer agents undergo β-scission reactions, they are limited to producing oligomers having homomethacrylate backbones.

In the *European Polymer Journal*, Volume 8, pages 321–328 (1972), Feit describes a multistep synthesis technique for preparing terminally-unsaturated oligomers and co-oligomers of vinyl monomers having electronegative groups. The process described therein requires a base-catalyzed addition of an acetic acid ester derivative to an activated olefin, followed by hydrolysis of one ester group, followed by a Mannich reaction to introduce a terminal double bond. This three step process is repeated to prepare a terminally-unsaturated oligomer with one additional mer. This process suffers the drawback of being fairly complex, expensive and time-consuming.

U.S. Pat. No. 5,710,227 discloses a high temperature, continuous polymerization process for preparing terminally unsaturated oligomers which are formed from acrylic acid and its salts, and acrylic acid and its salts with other ethylenically unsaturated monomers. The high temperature, continuous polymerization process solves many of the problems associated with previously known methods for preparing terminally-unsaturated oligomers formed from acrylic acid. However, the neat form of many of the acrylic acid products are solid and, thus, require the addition of a solvent to handle and use the products.

U.S. Pat. No. 4,356,288 discloses the preparation of terminally-unsaturated oligomers formed from esters of acrylic acid having a degree of polymerization of about 6–30 by an anionic polymerization reaction carried out in the presence of a catalytic amount of an alkoxide anion. The method is relatively complex. Because the method is inhibited by the presence of moisture (lowering yield and uniformity of the final product), it is not a viable commercial process.

In *Chemical Engineering at Supercritical Fluid Conditions*, pages 515–533 (1983), Metzger et al. disclose the dimerization and trimerization of methyl acrylate in benzene at a pressure of 200 bars and temperatures of 340–420° C. in a flow reactor with a residence time of 5 minutes.

The present invention seeks to overcome the problems associated with the previously known methods for preparing oligomers by providing a polymerization process that is not limited to forming oligomers having only a homomethacrylate backbone or a carboxylic acid-containing monomer residue backbone and that does not require water or other solvent in the manufacture or use of the oligomer. The present invention also provides an oligomer free of metal, salt and surfactant contaminants, that, due to its purity and composition, is not water sensitive or discolored and is liquid when provided neat.

STATEMENT OF THE INVENTION

The invention is directed to a continuous process for preparing terminally-unsaturated and fully saturated oligomers which do not contain, as polymerized units, carboxylic acid-containing monomers, including the steps of:

(1) forming a reaction mixture, substantially free of carboxylic-acid monomers and their salts, containing:
   (i) 0.5 to 99.95% by weight of the reaction mixture of at least one ethylenically unsaturated monomer; and (ii) 0.05 to 25% by weight, based on the weight of the monomer, of at least one free-radical initiator; and (2) continuously passing the reaction mixture through a heated zone wherein the reaction mixture is maintained at a temperature of at least 150° C. and a pressure of at least 30 bars for from 0.1 seconds to 4 minutes to form terminally-unsaturated oligomers.

In addition, the invention is directed to a process for preparing fully saturated oligomers including the further step of hydrogenating the terminally unsaturated oligomer. The invention is also directed to processes for forming oligomers of vinyl acetate and oligomers of vinyl alcohol.

The process of the invention is useful for preparing oligomers of the formula:

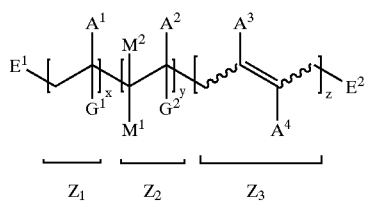

where

A, $A^1$ and $A^2$=
independently selected from —H;
$C_1$–$C_{50}$ straight-chain or branched alkyl, optionally substituted with a Y group;
$C_2$–$C_{50}$ straight-chain or branched alkenyl containing 1–5 double bonds, optionally substituted with 1–2 Y groups;
$C_5$–$C_8$ cycloalkyl, $C_5$–$C_8$ cycloalkenyl;
phenyl, $(CH_2)_m$-phenyl, 1- or 2-naphthyl;
—(C=O)H; —C(OR$^1$)$_2$H;
—(C=O)R$^1$, —(C=O)CF$_3$; —C(OR$^1$)$_2$R$^1$;
—(C=O)OR, —O(C=O)R$^1$; —(C=O)Cl;
—O(C=O)OR$^1$; —OR;
—(C=O)NH$_2$, —(C=O)NHR$^1$, —(C=O)N(R$^1$)$_2$, —NH(C=O)R$^1$, —NH(C=O)H, —(C=O)NH(CH$_2$)$_m$(NH$_3$)$^{(+)}$(X)$^{(-)}$, —(C=O)NH(CH$_2$)$_m$(NR$^1$)$_2$;
—Si(OR$_1$)$_3$, —Si(OR$^1$)$_2$R$^1$, —Si(OR$^1$)(R$^1$)$_2$, —Si(R$^1$)$_3$;
—F, —Cl, —Br, —I;
—C≡N; oxiranyl;
—NH(C=O)NH$_2$, —NH(C=O)NHR$^1$, —NH(C=O)N(R$^1$)$_2$;

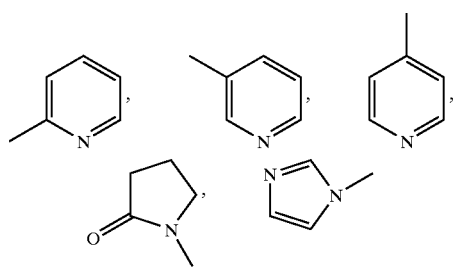

—CH$_2$C$_n$F$_{2n+1}$, —CH$_2$CH$_2$C$_n$F$_{2n+1}$, —CH(CF$_3$)$_2$, —CH$_2$C$_n$F$_{2n}$H, —CH$_2$CH$_2$C$_n$F$_{2n}$H;
—P(=O)(OR$^1$)$_3$; —S(=O)$_2$(OR$^1$); —S(=O)$_2$R$^1$;

$A^3$, $A^4$=independently selected from —H, —F, —Cl, —Br, R$^{1-}$;

$E^1$, $E^2$=independently selected from —H,

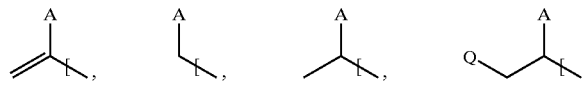

$G^1$, $G^2$=independently selected from —H, —CH$_3$, —(CH$_2$)$_m$CO$_2$R$^1$, —F, —Cl, —Br, —I;
$M^1$, $M^2$=independently selected from —H, —C≡N, —(C=O)OR$^1$, —F, —Cl, —Br, —I;
Q=$C_1$–$C_8$ straight-chain or branched alkyl, —OR$^3$, residue from radical decomposition of azo initiators (azonitrile, azoamidine, cyclic azoamidine, azoamide, azoalkyl classes) such as —C(R$^4$)$_2$C≡N;
R=
$C_1$–$C_{50}$ straight-chain or branched alkyl, $C_2$–$C_{50}$ straight-chain or branched alkenyl containing 1–5 double bonds;
$C_5$–$C_8$ cycloalkyl, $C_5$–$C_8$ cycloalkenyl;
phenyl, $(CH_2)_m$-phenyl, 1- or 2-naphthyl, -4-benzoylphenyl (where any phenyl group may be substituted with up to 2 R$^2$), anthracenyl, anthracenylmethyl;
—(CH$_2$)$_m$O(C=O)R$^1$, —(CH$_2$)$_m$(C=O)OR$^1$;
—(CH$_2$)$_m$(C=O)R$^1$;
—(CH$_2$)$_m$(C=O)NH$_2$, —(CH$_2$)$_m$(C=O)NHR$^1$, —(CH$_2$)$_m$(C=O)NH(R$^1$)$_2$;
—(CH$_2$)$_m$N(R$^1$)$_2$, —(CH$_2$)$_m$NH$_3^{(+)}$X$^{(-)}$;
—(CH$_2$)$_m$OR$^1$, —(CH$_2$CH$_2$O)$_m$R$^1$, —(CH$_2$CH(CH$_3$)O)$_m$R$^1$, -2-tetrahydrofuranyl;
—(CH$_2$)$_m$N=C=O;
—CH$_2$C$_n$F$_{2n+1}$, —CH$_2$CH$_2$C$_n$F$_{2n+1}$, —CH(CF$_3$)$_2$, —CH$_2$C$_n$F$_{2n}$H, —CH$_2$CH$_2$C$_n$F$_{2n}$H;

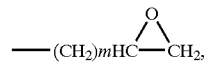

linear alkanes containing 1–5 epoxy groups derived from (poly)unsaturated vegetable oils;
—(CH$_2$)$_p$OH, —(CH$_2$CH$_2$O)$_m$H, —[CH$_2$CH(CH$_3$)O]$_m$H;
—(CH$_2$)$_m$Si(OR$^1$)$_3$, —(CH$_2$)$_m$Si(R$^1$)(OR$^1$)$_2$, —(CH$_2$)$_m$Si(R$^1$)$_2$OR$^1$, —(CH$_2$)$_m$Si(R$^1$)$_3$;

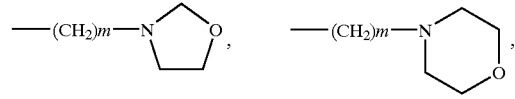

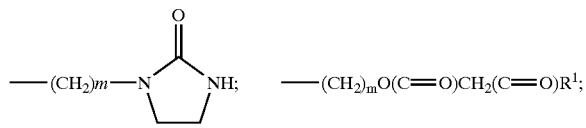

R$^1$=independently selected from $C_1$–$C_8$ straight chain or branched alkyl where (R$^1$)$_2$ may constitute a $C_5$–$C_8$ cycloalkyl group; phenyl, —CH$_2$phenyl;
R$^2$=$C_1$–$C_6$ straight chain or branched alkyl, $C_1$–$C_6$ straight chain or branched alkoxy, —CHO, —(C=O)OR1, —N(R$^1$)$_2$, —NO$_2$, —(C=O)N(R$^1$)$_2$, —CF$_3$, —(C=O)R$^1$; —F, —Cl —Br, —I;
R$^3$=—H, $C_1$–$C_8$ straight chain or branched alkyl, —R$^1$(C=O), —R$^1$(C=O)O;
R$^4$=$C_1$–$C_{18}$ straight-chain alkyl, $C_5$–$C_8$ cycloalkyl wherein the two adjacent R$^4$ groups may together form a 5–8 membered ring, $C_1$–$C_4$ alkoxy-substituted straight-chain or branched $C_1$–$C_8$ alkyl groups;

$X^{(-)}$=—$F^{(-)}$, —$Cl^{(-)}$, —$Br^{(-)}$, —$I^{(-)}$, —$HSO_4^{(-)}$, —$H_2PO_3^{(-)}$;

Y=—OH, —F, —Cl, —Br, —I, —$NH_2$, —$N(R^1)_2$;

m=1–8 n=1–18 p=2–8 x=0–49 y=0–49 z=0–49 x+y+z≦49.

The invention is also directed to a mixture that contains:

(1) about 50 to 90% by weight, based on the weight of the mixture, of a first oligomer having terminal unsaturation of Formula (1), where at least one of $E^1$ and $E^2$ is an endgroup of the formula:

(II)

and when only one of $E^1$ and $E^2$ is an endgroup of Formula (II) then the other endgroup is selected independently from H,

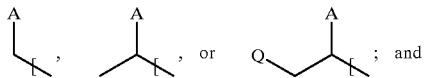

; and (2) about 10 to 50% by weight, based on the weight of the mixture, of a second oligomer having no terminal unsaturation of Formula (I), wherein $E^1$ and $E^2$ are independently selected from

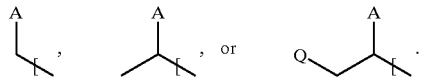

.

DETAILED DESCRIPTION OF THE INVENTION

As used herein, the term "(meth)acrylate" refers to methacrylate and acrylate, the term "(meth)acrylic" refers to methacrylic and acrylic and the term "(meth)acrylamide" refers to methacrylamide and acrylamide. As used herein, the term "substantially free" means less than 0.5% by weight. As used herein, the term "ambient conditions" means at a temperature of 20° C.–40° C. and at a pressure of 1 bar. As used herein, the term "homooligomer" means an oligomer containing the same monomer units and the term "co-oligomer" means an oligomer containing at least two different monomer units. As used herein, the term "neat" means a composition that contains only the oligomer and is substantially free of solvent and other additives. As used herein, the phrase "carboxylic-acid containing monomers and their salts" means monoethylenically unsaturated monocarboxylic acids, and the alkali metal, alkaline earth metal, and ammonium salts thereof, and monoethylenically unsaturated dicarboxylic acids, and the alkali metal, alkaline earth metal, and ammonium salts thereof, and the anhydrides of the cis-dicarboxylic acids.

The first step of the process of the invention is forming a reaction mixture, substantially free of carboxylic acid-containing monomers and their salts, containing:

(a) from 0.5 to 99.95% by weight of the reaction mixture of at least one ethylenically unsaturated monomer; and (b) from 0.05 to 25% by weight, based on the weight of the ethylenically unsaturated monomer, of at least one free-radical initiator.

Preferably, the reaction mixture contains 10% to 99.9% by weight, and most preferably, 50% to 98% by weight, based on the weight of the reaction mixture, of at least one ethylenically unsaturated monomer. Preferably, the reaction mixture contains 0.1% to 5% by weight, and most preferably, 1% to 2% by weight, based on the weight of the ethylenically unsaturated monomer, of at least one free-radical initiator.

The process of the invention is suitable for polymerizing any ethylenically unsaturated monomer, except carboxylic acid-containing monomers and their salts. Suitable monomers include, but are not limited to, n-alkyl(meth)acrylates, such as methyl acrylate, butyl methacrylate, octadecyl acrylate;

branched alkyl(meth)acrylates, such as isopropyl methacrylate, 2-ethyl hexyl acrylate, isobornyl methacrylate;

cycloalkyl(meth)acrylates, such as cyclopentyl methyl acrylate, cyclohexyl methacrylate;

straight chain or branched haloalkyl(meth)acrylates, such as 2,2,2-trifluoroethyl acrylate, hexafluoroisopropyl methacrylate, 2,2,3,3,4,4,5,5,6,6,7,7,8,8,8-pentadecafluorooctyl acrylate;

aromatic alkyl(meth)acrylates, such as benzyl acrylate, 4-chlorophenethyl methacrylate;

aromatic (meth)acrylates, such as phenyl acrylate, 4-benzoyl phenyl acrylate;

hydroxyalkyl(meth)acrylates, such as 2-hydroxyethyl acrylate, 4-hydroxybutyl methacrylate;

heterocyclyl(meth)acrylates, such as 3-oxazolidinyl ethyl methacrylate, N-ethyl-ethylene ureido methacrylate;

aminoalkyl(meth)acrylates, such as N,N-dimethyl aminoethyl acrylate and acid salts of 2-aminoethyl acrylate, N,N-diethyl aminopropyl methacrylate;

ether-containing (meth)acrylates, such as ethoxyethoxyethyl acrylate, 2-tetrahydrofuranyl acrylate, ethyl ether of a polyalkoxylated ester of methacrylic acid;

silicon-containing (meth)acrylates, such as trimethoxysilylpropyl acrylate, diethoxymethylsilylpropyl methacrylate, isopropoxydimethylsilylpropyl acrylate;

(meth)acrylamides, such as N-methyl acrylamide, N,N-dimethylaminopropyl methacrylamide;

epoxide-containing (meth)acrylates, such as glycidyl (meth)acrylate, (meth)acrylates derived from partially or completely epoxidized (poly)unsaturated vegetable oils;

unsaturated alkyl(meth)acrylates, such as vinyl acrylate, allyl methacrylate, 2,4 hexadienyl methacrylate;

(meth)acrylate esters derived from (poly)unsaturated vegetable oils; terminal alkenes, such as ethylene, 1-hexene, 3-vinyl cyclohexene;

aralkenes, such as styrene, 4-methyl styrene, α-methyl styrene, 4-methoxy styrene, 4-benzoyl styrene, 4-N,N-dimethylaminostyrene;

heterocyclyl alkenes, such as 2,-3, or 4-vinyl pyridines and N-vinyl imidazole;

dienes, such as butadiene, isoprene, vinylidene chloride, vinyl fluoride;

vinyl halides, such as vinyl chloride, tetrafluoroethylene;

vinyl esters, such as vinyl acetate, vinyl benzoate;

vinyl ketones, such as methyl vinyl ketone;

aldehyde containing vinyl functionality, such as (meth) acrolein and their acetal derivatives;

epoxyalkenes, such as 3,4-epoxybut-1-ene;

vinyl monomers, such as (meth)acrylonitrile, N-vinyl formamide, N-vinyl acetamide, fumaronitrile;

vinylsilanes and alkoxyvinylsilanes, such as vinyltrimethylsilane, vinyltrimethoxy silane, vinyldiethoxymethylsilane;

unsaturated diesters, such as dimethylmaleate, dibutylfumarate, diethyl itaconate;

functional (meth)acrylates, such as isocyanatoethyl methacrylate, acryloylchloride, aceto acetoxylethyl methacrylate Preferred ethylenically unsaturated monomers include those monomers whose neat homooligomer of a degree of polymerization of about 5 to about 10 is a liquid under ambient conditions.

Suitable initiators for carrying out the processes of the present invention are any conventional free-radical initiators including, but are not limited to, hydrogen peroxide, certain alkyl hydroperoxides, dialkyl peroxides, peresters, percarbonates, persulfates, peracids, oxygen, ketone peroxides, azo initiators and combinations thereof Specific examples of some suitable initiators include hydrogen peroxide, oxygen, t-butyl hydroperoxide, di-tertiary butyl peroxide, tertiary-amyl hydroperoxide, methylethyl ketone peroxide and combinations thereof.

The monomers may be polymerized as dilute solutions, although the process does not require solvent, nor is the use of solvents preferred. The reaction mixture may contain one or more solvents at a level of from 0% to 99.5% by weight of the reaction mixture, preferably from 30% to 97% by weight of the reaction mixture, and most preferably from 50% to 95% by weight of the reaction mixture. As the relative amount of one or more solvents in the reaction mixture decreases, particularly below 60%, the molecular weight and the polydispersity of the resulting oligomer mixture increases. Suitable solvents for the process of the present invention are capable of dissolving the one or more monomers, especially under the supercritical fluid conditions of the process, and the oligomers formed therefrom. Suitable solvents for the present invention include, for example, ethers such as tetrahydrofuran, ketones such as acetone; esters such as ethyl acetate; alcohols such as methyl alcohol and butyl alcohol; alkanes such as hexane and heptane; aromatic hydrocarbons such as benzene, toluene and xylene; supercritical fluids such as carbon dioxide; water; and mixtures thereof. Supercritical fluids such as carbon dioxide are particularly useful because the solvent readily is stripped from the product and may be recycled.

In the second step of the process of the present invention, the reaction mixture is continuously passed through a heated zone, wherein the reaction mixture is maintained at a temperature of at least 150° C. under elevated pressure. Once the reaction mixture is formed, it is preferable to have the passing reaction mixture reach the polymerization temperature as rapidly as possible. Preferably, the reaction mixture reaches the polymerization temperature within 2 minutes, more preferably within 1 minute, most preferably within 30 seconds. Prior to reaching the reaction temperature, the reaction mixture may be at any suitable temperature, preferably at a temperature of from room temperature to 450° C., most preferably from a temperature of from room temperature to 60° C. to 400° C. The oligomerization is conducted at a temperature of at least 150° C., and is preferably conducted at a temperature in the range of from 200° C. to 500° C., and most preferably at a temperature in the range of from 275° C. to 450° C. At temperatures below 150° C., the molecular weight of the oligomer increases and the relative amount of by-products, particularly non-terminally unsaturated compounds, increases.

The oligomerization at the elevated temperatures of the process of the invention is rapid. Thus, the reaction mixture can be maintained at the polymerization temperature for as little as 0.1 seconds up to 4 minutes, preferably from 0.5 seconds to 2 minutes, most preferably from 1 second to 1 minute. Under extended periods of time at which the reaction mixture is exposed to the polymerization temperature, the yield of terminally unsaturated oligomer decreases. However, extended periods at the polymerization temperature have been found to have little effect on both the conversion of monomer and the molecular weight of the products formed.

The elevated temperatures of the polymerization require that the polymerization reactor be equipped to operate at elevated pressure of at least 30 bars to maintain the contents of the reactor as a fluid at the reaction temperature. In general, it is preferred to conduct the polymerization at from 70 bars to 350 bars, and more preferably at from 200 bars to 300 bars.

In the process of the present invention, the ethylenically unsaturated monomers, initiator and, optionally, solvent are combined to form a reaction mixture. The order of combining the components of the reaction mixture is not critical to the process of the present invention. In one embodiment of the present invention, it may be desirable to use one or more solvents, heat the one or more solvents to an elevated temperature, and add the one or more monomers and the at least one initiator to the heated solvent to form the reaction mixture. It is preferred to add the initiator last. The reaction mixture can be formed at a temperature below, at or above the oligomerization temperature. In one embodiment of the invention, it may be desirable to add an additional amount of solvent to the oligomer product while the oligomer product is at an elevated temperature to maintain desirable fluidity and viscosity properties of the oligomer product.

Reactors suitable for use in the process of invention include tubular reactors having no moving parts and of any cross-sectional shape that permit continuous, steady state flow and that may operate under elevated temperatures and pressures. Such reactors are typically made from inert materials, such as stainless steel or titanium. The reactor may be of any length and cross-sectional dimension that permits effective temperature and pressure control.

Depending upon the final application of the oligomeric products of the invention, the reaction mixture may optionally contain metal ions, such as copper, nickel or iron ions or combinations thereof. However, their presence is not preferred.

The process of the present invention generally results in a relative conversion of the monomers into oligomer product of from 10% to greater than 95% relative to the initial amount of the one or more monomers present in the reaction mixture. If residual monomer levels in the oligomer mixture are unacceptably high for a particular application, their levels can be reduced by any of several techniques known to those skilled in the art, including rotary evaporation, distillation, and vacuum distillation. Preferably, any residual monomers which may be present in the oligomer mixture are distilled or "stripped" and recycled for later use.

The process of the present invention results in oligomers having low molecular weights and narrow polydispersities. Furthermore, embodiments of the process result in products that do not require the removal of organic solvents (if none were used in the process) and are not contaminated with high levels of salt. The process of the present invention may be used to produce oligomers having number average molecular weights below 5,000, preferably below 3,000, and most preferably from 200 to 1,000.

The process of the invention may contain an optional third step wherein the terminal unsaturation of the terminally unsaturated oligomers is removed by hydrogenation under conditions known to those skilled in the art, with or without solvent. Preferably, the hydrogenation may be carried out utilizing a wide variety of hydrogenation catalysts on an alkaline metal salt support. Preferred metal catalysts include those comprising metals selected from groups 3, 4, 5, 6, 7, 8, 9, 10, 11 or 12 of the Periodic Table of Elements as published in *Chemical and Engineering News* 63(5), 27, 1985, is preferably present in the reaction at a ratio of 0.01 to 5.0, and preferably 0.02 to 2.0 grams of catalyst per gram of unsaturated oligomer. The degree of hydrogenation is determined from proton NMR measurements at 25° C. using oligomer solutions in $CDCl_3$ with TMS as the internal reference. Upon hydrogenation the resonances associated with olefinic protons are converted to aliphatic protons. Thus the saturation efficiency can be measured by analyzing the remaining olefinic proton resonances.

The process of the invention is useful for preparing oligomers of the formula:

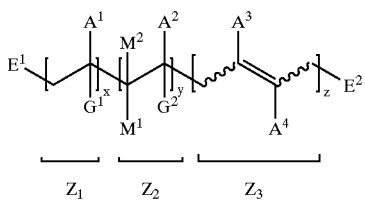

where

A, $A^1$ and $A^2$=
  independently selected from —H;
  $C_1$–$C_{50}$ straight-chain or branched alkyl, optionally substituted with a Y group;
  $C_2$–$C_{50}$ straight-chain or branched alkenyl containing 1–5 double bonds, optionally substituted with 1–2 Y groups;
  $C_5$–$C_8$ cycloalkyl, $C_5$–$C_8$ cycloalkenyl;
  phenyl, $(CH_2)_m$-phenyl, 1- or 2-naphthyl;
  —C(=O)H; —C(OR$^1$)$_2$H;
  —C(=O)R$^1$, —C(=O)CF$_3$; —C(OR$^1$)$_2$R$^1$;
  —C(=O)OR, —O(C=O)R$^1$; —C(=O)Cl;
  —O(C=O)OR$^1$; —OR;
  —C(=O)NH$_2$, —C(=O)NHR$^1$, —C(=O)N(R$^1$)$_2$, —NH(C=O)R$^1$, —NH(C=O)H, —C(=O)NH(CH$_2$)$_m$(NH$_3$)$^{(+)}$(X)$^{(-)}$, —C(=O)NH(CH$_2$)$_m$(NR$^1$)$_2$;
  —Si(OR$^1$)$_3$, —Si(OR$^1$)$_2$R$^1$, —Si(OR$^1$)(R$^1$)$_2$, —Si(R$^1$)$_3$;
  —F, —Cl, —Br, —I;
  —C≡N; oxiranyl;
  —NH(C=O)NH$_2$, —NH(C=O)NHR$^1$, —NH(C=O)N(R$^1$)$_2$;

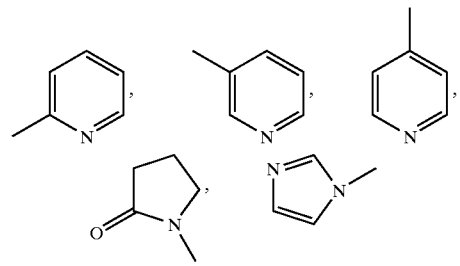

—CH$_2$C$_n$F$_{2n+1}$, —CH$_2$CH$_2$C$_n$F$_{2n+1}$, —CH(CF$_3$)$_2$, —CH$_2$C$_n$F$_{2n}$H, —CH$_2$CH$_2$C$_n$F$_{2n}$H;
—P(=O)(OR$^1$)$_3$; —S(=O)$_2$(OR$^1$); —S(=O)$_2$R$^1$;

$A^3$, $A^4$=independently selected from —H, —F, —Cl, —Br, R$^1$;

$E^1$, $E^2$=independently selected from —H,

$G^1$, $G^2$=independently selected from —H, –CH$_3$, —(CH$_2$)$_m$ CO$_2$R$^1$, —F, —Cl, —Br, —I;

$M^1$, $M^2$=independently selected from —H, —C≡N, —(C=O)OR$^1$, —F, —Cl, —Br, —I;

Q=$C_1$–$C_8$ straight-chain or branched alkyl, —OR$^3$, residue from radical decomposition of azo initiators (azonitrile, azoamidine, cyclic azoamidine, azoamide, azoalkyl classes) such as —C(R$^4$)$_2$C≡N;

R=
  $C_1$–$C_{50}$ straight-chain or branched alkyl,
  $C_2$–$C_{50}$ straight-chain or branched alkenyl containing 1–5 double bonds;
  $C_5$–$C_8$ cycloalkyl, $C_5$–$C_8$ cycloalkenyl;
  phenyl, $(CH_2)_m$-phenyl, 1- or 2-naphthyl, -4-benzoylphenyl (where any phenyl group may be substituted with up to 2 R$^2$), anthracenyl, anthracenylmethyl;
  —(CH$_2$)$_m$O(C=O)R$^1$, —(CH$_2$)$_m$(C=O)OR$^1$;
  —(CH$_2$)$_m$(C=O)R$^1$;
  —(CH$_2$)$_m$(C=O)NH$_2$, —(CH$_2$)$_m$(C=O)NHR$^1$, —(CH$_2$)$_m$(C=O)NH(R$^1$)$_2$;
  (CH$_2$)$_m$N(R$^1$)$_2$, —(CH$_2$)$_m$NH$_3^{(+)}$X$^{(-)}$;
  —(CH$_2$)$_m$OR$^1$, —(CH$_2$CH$_2$O)$_m$R$^1$, —(CH$_2$CH(CH$_3$)O)$_m$R$^1$, -2-tetrahydrofuranyl;
  —(CH$_2$)$_m$N=C=O;
  —CH$_2$C$_n$F$_{2n+1}$, —CH$_2$CH$_2$C$_n$F$_{2n+1}$, —CH(CF$_3$)$_2$, —CH$_2$C$_n$F$_{2n}$H, —CH$_2$CH$_2$C$_n$F$_{2n}$H;

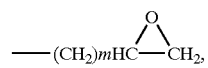

linear alkanes containing 1–5 epoxy groups derived from (poly)unsaturated vegetable oils;
—(CH$_2$)$_p$OH, —(CH$_2$CH$_2$O)$_m$H, —[CH$_2$CH(CH$_3$)O]$_m$H;
—(CH$_2$)$_m$Si(OR$^1$)$_3$, —(CH$_2$)$_m$Si(R$^1$)(OR$^1$)$_2$, —(CH$_2$)$_m$Si(R$^1$)$_2$OR$^1$, —(CH$_2$)$_m$Si(R$^1$)$_3$;

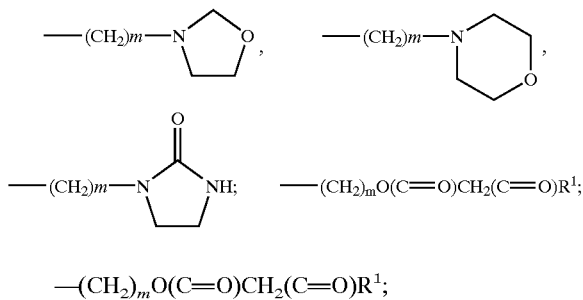

—(CH$_2$)$_m$O(C=O)CH$_2$(C=O)R$^1$;

R=independently selected from C$_1$–C$_8$ straight chain or branched alkyl where (R$^1$)$_2$ may constitute a C$_5$–C$_8$ cycloalkyl group; phenyl, —CH$_2$phenyl;

R$^2$=C$_1$–C$_6$ straight chain or branched alkyl, C$_1$–C$_6$ straight chain or branched alkoxy, —CHO, —(C=O)OR1, —N(R$^1$)$_2$, —NO$_2$, —(C=O)N(R$^1$)$_2$, —CF$_3$, —(C=O)R$^1$; —F, —Cl, —Br, —I;

R$^3$=—H, C$_1$–C$_8$ straight chain or branched alkyl, —R$^1$(C=O), —R$^1$(C=O)O;

R$^4$=C$_1$–C$_{18}$ straight-chain alkyl, C$_5$–C$_8$ cycloalkyl wherein the two adjacent R$^4$ groups may together form a 5–8 membered ring, C$_1$–C$_4$ alkoxy-substituted straight-chain or branched C$_1$–C$_8$ alkyl groups;

X$^{(-)}$=—F$^{(--)}$, —Cl$^{(-)}$, —Br$^{(-)}$, —I$^{(-)}$, —HSO$_4$$^{(-)}$, —H$_2$PO$_3$$^{(-)}$;

Y=—OH, —F, —Cl, —Br, —I, —NH$_2$, —N(R$^1$)$_2$;

m=1–8 n=1–18 p=2–8 x=0–49 y=0–49 z=0–49 x+y+z≦49.

It is understood that the residues of the monomers, Z$_1$, Z$_2$ and Z$_3$, in the oligomers of Formula (I) above may be randomly arranged to form alternating, random or block polymer structures. It is also understood that, not only are homooligomers and co-oligomers contemplated, but oligomers formed from more than two different types of monomers, such as low molecular weight terpolymers or "ter-oligomers", are also contemplated. In the broadest sense, it is understood that in the oligomer where there are up to 49 possible residues of monomers (whether of Z$_1$, Z$_2$ or Z$_3$ structure) the monomers are each independently selected such that it would be possible to form an oligomer from 49 different monomers.

The process of the present invention is useful for producing a mixture of oligomers containing:

(1) about 50 to 90% by weight, based on the weight of the mixture, of a first oligomer having terminal unsaturation of Formula (I), where at least one of E$^1$ and E$^2$ is an endgroup of the formula:

(II)

and when only one of E$^1$ and E$^2$ is an endgroup of Formula (II) then the other endgroup is selected independently from H,

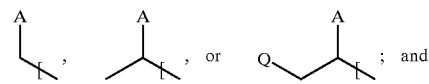

(2) about 10 to 50% by weight, based on the weight of the mixture, of a second oligomer having no terminal unsaturation of Formula (I), wherein E$^1$ and E$^2$ are independently selected from

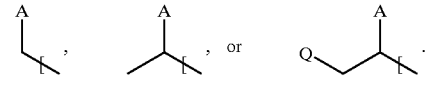

The mixture may optionally contain an oligomer formed by a chain-chain termination reaction.

Terminal unsaturation may be detected and measured by conventional techniques, including $^1$H NMR spectroscopy, $^{13}$C NMR spectroscopy, and bromine titration. The endgroups may be identified by conventional techniques, including MALDI-MS.

The terminally-unsaturated oligomers, fully saturated oligomers and mixtures of the invention may be supplied neat and flow under ambient conditions. The consistency of the products ranges from a thin, water-like fluid to a viscous, taffy-like fluid. Furthermore, they do not require the use of water or other solvents in the preparation or use and are substantially free of contaminants, including, salts, surfactants, metals and the like.

The oligomers of the invention may be used neat, provided in solvent or provided emulsified in water with at least one surfactant. The emulsified oligomer in water is preferred if the neat form of the oligomer is too viscous for use in an application. Suitable surfactants include conventional anionic, cationic, nonionic, amphoteric surfactants and mixtures thereof. The surfactant may be added at a level of at least 0.1% solids based on the weight of the oligomer. The emulsified composition may be prepared by mixing at least one surfactant, at least one oligomer, water and mixing vigorously. Other minor components, such as wetting agent, may be added to the emulsified composition. Alternatively, the emulsified composition may be prepared by adding the surfactant to the reaction mixture containing the ethylenically unsaturated monomer and initiator prior to oligomerization.

The oligomers of the invention are useful in many applications, including, for example, in binders and additives (surfactants, emulsifiers, rheology modifiers) for architectural coatings (paints, primers, lacquers, varnishes, stains, EIFS); in industrial coatings (including automotive finishes, metal finishes, printing inks and resins); in building products (wood coatings and binders, caulks, sealants, concrete modifiers and coatings, impregnants, polishes) in coatings and additives for paper, textiles, and nonwovens; in adhesives; in leather chemicals; in formulation chemicals (including detergents, dispersants, water treatment, scale inhibitors, suspension aids); in plastics and plastic additives (plasticizers, processing aids); in rubber and rubber additives (plasticizers, processing aids); in biocides and adjuvants; in agricultural chemicals and adjuvants; in electronic chemicals; in ion exchange resins (adsorbents and adsorbents); in oil additives; in solvents; in lubricants and hydraulic fluids; and the like.

EXAMPLES

The Equipment and General Procedures

A 10 foot long section of stainless steel tubing having an inner diameter of $\frac{1}{16}$th inch and a wall thickness of 0.050 inch was connected at one end to a high pressure pump (Hewlett Packard Model HP 1050 TI) and at another end to a back-pressure control device. Between the two ends, the section of tubing was coiled about a torus-shaped metal mandrel. The mandrel was situated above a primary coil of a transformer so that the coils of tubing and the mandrel functioned as secondary coils of the transformer. The coils of tubing were further equipped with one end of a temperature probe. The other end of the temperature probe was connected to a temperature controlling device. The temperature controlling device regulated the current supplied to the primary coil of the transformer which had the effect of regulating the heat of inductance imparted to the coiled steel tubing.

A reaction mixture was prepared by mixing solvent (if present), monomers, comonomers (if present) and initiator. Nitrogen was bubbled through the mixture while stirring. Under solvent-free conditions, the initiator and monomers/comonomers were separately fed into the reactor.

Solvent was pumped through the tubing via the high pressure pump at a rate of from 0.05 to 10 milliliters per minute ("ml/min"). The pressure was maintained at a level of from 200 bars to 350 bars. Current was supplied to the primary coil of the transformer to increase the temperature within the tubing to the desired polymerization temperature. After about 15 minutes, the solvent being pumped through the tubing was replaced by the reaction mixture which was continuously pumped through the tubing at the same rate, temperature and pressure. After allowing a suitable amount of time for the solvent to be cleared from the tubing, product was collected as the effluent from the back-pressure control device. When the reaction mixture was nearly gone, solvent was pumped through the tubing at the same rate, pressure and temperature as the reaction mixture. Solvent and residual monomer were removed on a rotary evaporator.

Terminal unsaturation was detected and measured by both $^1$H NMR spectroscopy and $^{13}$C NMR spectroscopy; endgroups were identified by MALDI-MS.

Examples 1–103 are oligomerizations conducted according to the general procedure outlined above. The reaction conditions and final properties of the oligomers are shown in Table 1.

TABLE 1

| Example | Ethylenically Unsaturated Monomer | Initiator (BOM)[1] | Solvent (w/w)[2] | Reactor Temperature (° C.) | % Conversion[3] | Mw/Mn[4] | dp[5] | Viscosity of neat oligomer (cps)[6] | $T_g$[7] (° C.) |
|---|---|---|---|---|---|---|---|---|---|
| 1 | EA | 1% dTBP | 50% in acetone | 375 | 99 | —/— | <7 | — | — |
| 2 | EA | 1% dTBP | 50% in acetone | 325 | 97 | 1670/640 | 7.3 | — | −54 |
| 3 | EA | 1% dTBP | 50% in acetone | 250 | 97 | 2900/1080 | 10.9 | — | — |
| 4 | BA | 2% dTBP | none | 300 | 82 | 2800/1000 | — | — | −72 |
| 5 | BA | 1% dTBP | 50% in heptane | 350 | 93–98 | — | — | — | −80→−75 |
| 6 | BA | 1% dTBP | 50% in ethyl acetate | 350 | 93–98 | — | — | — | −80→−75 |
| 7 | BA | 1% dTBP | 50% in acetone | 350 | 93–98 | — | — | — | −80→−75 |
| 8 | BA | 1% dTBP | 50% in heptane | 300 | 93–98 | — | 11.5 | — | −80→−75 |
| 9 | BA | 1% dTBP | 50% in ethyl acetate | 300 | 93–98 | — | 9.4 | — | −80→−75 |
| 10 | BA | 1% dTBP | 50% in acetone | 300 | 93–98 | — | 7.9 | — | −80→−75 |
| 11 | BA | 1% dTBP | 50% in heptane | 250 | 93–98 | — | 13.8 | — | −80→−75 |
| 12 | BA | 1% dTBP | 50% in ethyl acetate | 250 | 93–98 | — | 12.4 | — | −80→−75 |
| 13 | BA | 1% dTBP | 50% in acetone | 250 | 93–98 | — | 10.3 | — | −80→−75 |
| 14 | BA | 1% dTBP | 50% in heptane | 200 | 93–98 | — | 24.5 | — | −80→−75 |
| 15 | BA | 1% dTBP | 50% in ethyl acetate | 200 | 93–98 | — | 14.8 | — | −80→−75 |
| 16 | BA | 1% dTBP | 50% in acetone | 200 | 93–98 | — | 14.5 | — | −80→−75 |
| 17 | MA | 1% dTBP | 50% in acetone | 325 | 85 | — | 9.0 | — | −39 |
| 18 | LA | 1% dTBP | 50% in acetone/hexane | 350 | 99 | — | 15.8 | — | −14 (melting point) |
| 19 | stearyl acrylate | 1% dTBP | 50% in heptane | 375 | 98 | — | 20.8 | — | 19 |
| 20 | 2-EHA | 2% dTBP | 35% in acetone | 285 | 95 | 2727/1487 | — | cooking oil-like | −81 |
| 21 | i-bornyl acrylate | 1% dTBP | 50% in acetone | 325 | 96 | — | — | — | 7 |
| 22 | styrene | 2% dTBP | 30% in ethyl acetate | 350 | 46 | 1350/674 | 7.8 | — | −24 |
| 23 | styrene | 2% dTBP | 30% in ethyl acetate | 300 | 43 | 1880/920 | 17 | — | −7 |
| 24 | styrene | 2% dTBP | 50% in toluene | 350 | 73 | 2530/1360 | 14.7 | — | 1 |
| 25 | styrene | 2% dTBP | 50% in toluene | 300 | 64 | 3630/1950 | 21.1 | — | 13 |
| 26 | styrene | 2% dTBP | 50% in toluene | 250 | 56 | 4740/2310 | 25.1 | — | 13 |
| 27 | styrene | 2% dTBP | 50% in acetone | 325 | 42 | 4680/1950 | — | — | — |
| 28 | styrene | 2% dTBP | 50% in acetone | 275 | 44 | 4730/1850 | — | — | — |
| 29 | styrene | 2% dTBP | 50% in acetone | 225 | 53 | 6155/2450 | — | — | — |
| 30 | VAc | 4% dTBP | 50% in acetone | 280 | 62 | —/— | 8.7 | — | −7 |
| 31 | VAc | 2% dTBP | 50% in acetone | 225 | 58 | —/— | 10 | — | 6 |
| 32 | VAc[a] | 1% dTBP | 50% in acetone | 190 | 62 | 5546/1936 | 16 | — | 10 |
| 33 | VAc | 0.2% $H_2O_2$ | none | 325 | 40 | 7861/2331 | — | — | — |
| 34 | VAc | 0.2% $H_2O_2$ | none | 375 | 45 | 4933/1493 | — | — | — |
| 35 | VAc | 0.2% tBHP | none | 325 | 53 | 6217/1488 | — | — | — |
| 36 | VAc | 0.2% tBHP | none | 375 | 50 | 4151/1187 | — | — | — |
| 37 | VAc | 2% dTBP | 50% in acetone | 250 | — | 4734/1316 | — | taffy-like | — |

TABLE 1-continued

| Example | Ethylenically Unsaturated Monomer | Initiator (BOM)[1] | Solvent (w/w)[2] | Reactor Temperature (° C.) | % Conversion[3] | Mw/Mn[4] | dp[5] | Viscosity of neat oligomer (cps)[6] | $T_g$[7] (° C.) |
|---|---|---|---|---|---|---|---|---|---|
| 38 | VAc | 2% dTBP | 50% in acetone | 275 | — | 4310/1229 | — | taffy-like | — |
| 39 | VAc | 2% dTBP | 50% in acetone | 275 | 99 | 4800/1400* | — | taffy-like | — |
| 40 | methylvinyl ketone | 2% H₂O₂ | 50% in methyl alcohol | 250 | 82 | —/— | 13 | — | — |
| 41 | methylvinyl ketone | 2% H₂O₂ | 10% in methyl alcohol | 250 | 21 | —/— | 7 | — | — |
| 42 | methylvinyl ketone | 0.1% tBHP | 10% in methyl alcohol | 250 | 44 | —/— | 7 | — | — |
| 43 | methylvinyl ketone | 2% H₂O₂ | 10% in water | 375 | 70 | —/— | 5 | — | — |
| 44 | MMA | 2% dTBP | 50% in acetone | 200 | 20 | —/— | <5[9] | — | −37, −9 |
| 45 | MMA | 2% dTBP | 50% in acetone | 180 | 24 | —/— | <5[9] | — | −20, −1 |
| 46 | MMA | 2% dTBP | 50% in acetone | 160 | 27 | —/— | 30–40[9] | — | 68 |
| 47 Comparative | MMA | 2% dTBP | 50% in acetone | 140 | 22 | —/— | >60[9] | — | 98 |
| 48 | VTMO | 2% dTBP | 50% in acetone | 210 | 51 | 1150/800 | 7.4 | — | −76 |
| 49 | allyl alcohol | 2% H₂O₂ | 25% in water | 350 | 15–20 | —/— | — | — | 106 |
| 50 | allyl alcohol | 2% H₂O₂ | 25% in water | 300 | 15–20 | —/— | — | — | — |
| 51 | allyl alcohol | 2% H₂O₂ | 25% in water | 250 | 15–20 | —/— | — | — | — |
| 52 | allyl alcohol | 2% H₂O₂ | 25% in water | 200 | 15–20 | —/— | — | — | 106 |
| 53 | isoprene | 1% dTBP | 50% in toluene | 300 | 47 | 13700/3995 | — | — | — |
| 54 | isoprene | 1% dTBP | 50% in toluene | 225 | 31 | 22550/5738 | — | — | −59 |
| 55 | acrylamide | 1% H₂O₂ | 20% in water | 200 | 85–95 | —/— | — | — | 124 |
| 56 | EA/MMA[11] | 2% dTBP | 50% in acetone | 350 | 91/47 | —/— | 5 | — | — |
| 57 | EA/MMA[11] | 2% dTBP | 50% in acetone | 300 | 87/56 | —/— | 6 | — | — |
| 58 | EA/MMA[11] | 2% dTBP | 50% in acetone | 250 | 67/56 | —/— | 12 | — | −17 |
| 59 | EA/MMA[11] | 2% dTBP | 50% in acetone | 200 | 66/66 | —/— | — | — | — |
| 60 | 100 EA/0 MMA | 1% dTBP | 50% in acetone | 250 | 99/— | —/— | Mn = 1076 | — | −54 |
| 61 | 50 EA/50 MMA | 1% dTBP | 50% in acetone | 250 | 67/56 | —/— | Mn = 1270 | — | −17 |
| 62 | 25 EA/75 MMA | 1% dTBP | 50% in acetone | 300 | 91/41 | —/— | Mn = 830 | — | −56 |
| 63 | 25 EA/75 MMA | 1% dTBP | 50% in acetone | 250 | 79/37 | —/— | Mn = 900 | — | −44 |
| 64 | 25 EA/75 MMA | 1% dTBP | 50% in acetone | 200 | 54/35 | —/— | Mn = 1300 | — | −18 |
| 65 | 15 EA/85 MMA | 1% dTBP | 50% in acetone | 300 | 89/37* | —/— | — | — | −61 |
| 66 | 15 EA/85 MMA | 1% dTBP | 50% in acetone | 250 | 81/29* | —/— | — | — | −48 |
| 67 | 15 EA/85 MMA | 1% dTBP | 50% in acetone | 200 | 50/24* | —/— | Mn = 950 | — | −24 |
| 68 | EA/styrene[10] | 2% dTBP | 50% in acetone | 350 | 93/87 | —/— | Mn = 620 | — | — |
| 69 | EA/styrene[10] | 2% dTBP | 50% in acetone | 300 | 85/88 | —/— | Mn = 710 | — | — |
| 70 | EA/styrene[10] | 2% dTBP | 50% in acetone | 250 | 69/79 | —/— | Mn = 1209 | — | — |
| 71 | EA/styrene[10] | 2% dTBP | 50% in acetone | 200 | 63/74 | —/— | Mn = 1810 | — | — |
| 72 | MMA/styrene[10] | 2% dTBP | 50% in acetone | 320 | 50/70 | —/— | <5 | — | — |
| 73 | MMA/styrene[10] | 2% dTBP | 50% in acetone | 300 | 49/64 | —/— | <5 | — | — |
| 74 | MMA/styrene[10] | 2% dTBP | 50% in acetone | 280 | 47/61 | —/— | <5 | — | — |
| 75 | MMA/styrene[10] | 2% dTBP | 50% in acetone | 260 | 47/57 | —/— | <5 | — | — |
| 76 | BA/VAc[10] | 2% dTBP | 50% in acetone | 350 | 99/78 | —/— | Mn = 790 | — | −50 |
| 77 | BA/VAc[10] | 2% dTBP | 50% in acetone | 300 | 99/67 | —/— | Mn = 1056 | — | −53 |
| 78 | BA/VAc[10] | 2% dTBP | 50% in acetone | 250 | 99/64 | —/— | Mn = 1283 | — | −51 |
| 79 | BA/VAc[10] | 2% dTBP | 50% in acetone | 200 | 98/55 | —/— | Mn = 1740 | — | −42 |
| 80 | BA/VAc[10] | 2% dTBP | 50% in acetone | 150 | 94/41 | —/— | Mn = 5720 | — | −32 |
| 81 | MMA/VAc[10] | 2% dTBP | 50% in acetone | 300 | 73/69 | —/— | Mn = 782 | — | −9 |
| 82 | MMA/VAc[10] | 2% dTBP | 50% in acetone | 250 | 38/29 | —/— | Mn = 1252 | — | 4 |
| 83 | MMA/VAc[10] | 2% dTBP | 50% in acetone | 200 | 35/20 | —/— | Mn = 1436 | — | 7 |
| 84 | MMA/VAc[10] | 2% dTBP | 50% in acetone | 150 | 24/13 | —/— | Mn = 4470 | — | 25 |
| 85 | styrene/VAc[10] | 2% dTBP | 50% in acetone | 300 | 68/21 | —/— | Mn = 854 | — | −12 |
| 86 | styrene/VAc[10] | 2% dTBP | 50% in acetone | 250 | 59/14 | —/— | Mn = 1113 | — | 7 |
| 87 | styrene/VAc[10] | 2% dTBP | 50% in acetone | 200 | 63/14 | —/— | Mn = 1490 | — | 34 |
| 88 | styrene/VAc[10] | 2% dTBP | 50% in acetone | 150 | 30/10 | —/— | Mn = 2830 | — | 69 |
| 89 | 1:1 mole EA/VTMO | 2% dTBP | none | 300 | — | 1700/700 | — | 200 | −72 |
| 90 | 2:1 mole EA/VTMO | 2% dTBP | none | 300 | — | 1100/590 | — | 130 | −67 |
| 91 | BA/VTMO | 2% dTBP | none | 300 | — | 2100/900 | — | 190 | −75 |
| 92 | 2:1 mol EA/HEA | 2% dTBP | 50% in acetone | 330 | — | 3058/946[11] | — | syrup | −48 |
| 93 | 2:1 mol EA/HEA | 2% dTBP | 50% in acetone | 330 | — | 3700/1200[11] | — | 5100 at 25° C. | −45 |
| 94 | 4:1 mol EA/GA | 2% benzoyl peroxide | 30% in acetone | 260 | — | 1840/800 | ~8 | 8300 at 25° C. | −36 |
| 95 | 40 BA/60 allyl alcohol | 2% tBHP | 50% in butyl alcohol | 300 | 99/50 | 921/638 | — | — | — |
| 96 | 40 BA/60 allyl alcohol | 2% tBHP | 50% in butyl alcohol | 225 | 78/41 | 1580/1030 | — | — | — |

TABLE 1-continued

| Example | Ethylenically Unsaturated Monomer | Initiator (BOM)[1] | Solvent (w/w)[2] | Reactor Temperature (° C.) | % Conversion[3] | Mw/Mn[4] | dp[5] | Viscosity of neat oligomer (cps)[6] | $T_g$[7] (° C.) |
|---|---|---|---|---|---|---|---|---|---|
| 97 | 40 BA/60 allyl alcohol | 2% tBHP | 50% in butyl alcohol | 200 | 60/36 | 2208/1391 | — | — | — |
| 98 | 45 VAc/28 BA/25 Sty | 2% tBHP | none | 200 | 23/78/84 | 6086/1448 | — | — | — |
| 99 | 45 VAc/28 BA/25 Sty | 2% tBHP | none | 250 | 20/74/80 | 4386/1015 | — | — | — |
| 100 | 45 VAc/28 BA/25 Sty | 2% tBHP | none | 275 | 26/83/87 | 3786/914 | — | — | — |
| 101 | 45 VAc/28 BA/25 Sty | 2% tBHP | none | 300 | 34/93/94 | 3288/810 | — | — | — |
| 102 | 45 VAc/28 BA/25 Sty | 2% tBHP | none | 325 | 45/97/97 | 2865/683 | — | — | — |
| 103 | 45 VAc/28 BA/25 Sty | 2% tBHP | none | 350 | 53/99/98 | 2435/560 | — | — | — |

Abbreviations used in table:
EA = ethyl acrylate; BA = butyl acrylate; MA = methyl acrylate; LA = lauryl acrylate; VAc = vinyl acetate MMA = methyl methacrylate; VTMO = vinyltrimethoxysilane; HEA = hydroxyethyl acrylate; GA = glycidyl acrylate; dTBP = di-t-butyl peroxide; tBHP = tertbutylhydroperoxide; $H_2O_2$ = hydrogen peroxide
[1] Based on weight of monomer
[2] Percentage of weight of solvent based on weight of total composition
[3] Conversion was measured as a function of product solids, and was also determined by residual monomer analysis using high pressure liquid chromatography or gas chromatography
[4] Measured by gel permeation chromatography (GPC) using an oligomeric butyl acrylate or oligomeric ethyl acrylate standard unless specifically stated otherwise
[5] Degree of polymerization as measured by $^1$H NMR unless specifically stated otherwise.
[6] Viscosity measured by a Brookfield viscometer at 25° C.
[7] Measured by differential scanning calorimetry at a rate of 20° C./minute unless specifically stated otherwise
[8] Neat oligomeric product was subsequently added to methanol and boiled with 1% sodium hydroxide until oligomeric vinyl alcohol precipitated. After solvent removal, the degree of hydrolysis was determined at >90% with Mw/Mn = 2850/990 (calculated from oligomeric vinyl acetate). The $T_g$ was measured at 40° C. (conventional oligomeric vinyl acetate has Tg of 80° C.). Oligomeric vinyl acetate readily dissolves to >40% solids in water with gentle stirring (conventional oligomeric vinyl acetate requires prolonged heating to dissolve).
[9] Estimated from $T_g$ and a published plot of $T_g$ v. dp. [Haggard et al., Prog. Org. Coatings, Volume 12, No. 1, page 19(1984)]
[10] 50:50 mole ratio
[11] Deteremined using pMMA standards and converted to oBA standards using the following equations (assuming linearity and accuracy at higher molecular weights)
$M_{w(oBA\ std)} = 432 + 0.447\ M_{w(pMMA\ std)}$
$M_{n(oBA\ std)} = 169 + 0.713\ M_{n(pMMA\ std)}$ All of the examples of the invention were liquid, ranging from low viscosity to high viscosity, when provided neat, whether or not the reaction mixture contained the optional solvent during the process of manufacture.

While only a few embodiments of the invention have been shown and described herein, it will become apparent to those skilled in the art that various modifications and changes can be made in the process and compositions without departing from the scope of the present invention.

What is claimed is:

1. A process for forming oligomers, comprising the steps of:
   (1) forming a reaction mixture, substantially free of solvent and carboxylic acid-monomers and their salts, comprising:
      (i) 0.5 to 99.95% by weight, based on the weight of said reaction mixture, of at least one ethylenically-unsaturated monomer; and
      (ii) 0.05 to 25% by weight, based on the weight of said ethylenically-unsaturated monomer, of at least one free-radical initiator; and
   (2) continuously passing said reaction mixture through a heated zone wherein said reaction mixture is maintained at a temperature of at least 150° C. and a pressure of at least 30 bars for from 0.1 seconds to 4 minutes to form terminally-unsaturated oligomers, wherein the reaction is conducted in a tubular reactor having no moving parts.

2. A process for forming terminally-unsaturated oligomers having a degree of polymerization of at least 4, comprising the steps of:
   (1) forming a reaction mixture, substantially free of carboxylic-acid containing monomers and their salts, comprising:
      (i) 0.5 to 99.95% by weight, based on the weight of said reaction mixture, of at least one ethylenically-unsaturated monomer; and
      (ii) 0.05 to 25% by weight, based on the weight of said ethylenically-unsaturated monomer, of at least one free-radical initiator; and
   (2) continuously passing said reaction mixture through a heated zone wherein said reaction mixture is maintained at a temperature of at least 150° C. and a pressure of from 70 bars to 350 bars for from 0.1 seconds to 4 minutes to form terminally-unsaturated oligomers.

3. A process for forming terminally-unsaturated oligomers having a degree of polymerization of at least 4, comprising the steps of:
   (1) forming a reaction mixture, substantially free of carboxylic-acid containing monomers and their salts, comprising:
      (i) 0.5 to 99.95% by weight, based on the weight of said reaction mixture, of at least one ethylenically-unsaturated monomer; and
      (ii) 0.05 to 25% by weight, based on the weight of said ethylenically-unsaturated monomer, of at least one free-radical initiator; and
   (2) continuously passing said reaction mixture through a heated zone wherein said reaction mixture is maintained at a temperature of at least 150° C. and a pressure of at least 30 bars for from 0.1 seconds to 4 minutes to form terminally-unsaturated oligomers; wherein step (2) is conducted in a tubular reactor having no moving parts.

4. The process of claims 1 or 2, wherein said reaction mixture comprises at least two different ethylenically-unsaturated monomers.

5. The process of claims 1 or 2, wherein said reaction mixture comprises at least three different ethylenically-unsaturated monomers.

6. The process of claim 2, wherein said reaction mixture further comprises 0% to 99.5% by weight solvent.

7. The process of claim 6, wherein said solvent is at least one solvent selected from the group consisting of tetrahydrofuran, acetone, ethyl acetate, methyl alcohol, butyl alcohol, hexane, heptane, benzene, toluene, xylene, carbon dioxide, water, and mixtures thereof.

8. The process of claims 1 or 2, further comprising the step of:
(3) hydrogenating said terminally-unsaturated oligomers.

9. The process of claims 2 or 3 wherein said heated zone is maintained at a temperature of from 200° C. to 500° C.

10. The process of claims 2 or 3 wherein said heated zone is maintained at a temperature of from 275° C. to 450° C.

11. The process of claim 3 wherein said heated zone is maintained at a pressure of from 70 bars to 350 bars.

12. The process of claims 2 or 3 wherein said heated zone is maintained at a pressure of from 200 bars to 300 bars.

13. The process of claims 2 or 3 wherein said reaction mixture is maintained in said heated zone for from 0.5 seconds to 2 minutes.

14. The process of claims 2 or 3 wherein said reaction mixture is maintained in said heated zone for from 1 second to 1 minute.

15. A process for forming oligomers of vinyl acetate, comprising the steps of:
(1) forming a reaction mixture, substantially free of carboxylic-containing monomers and their salts, comprising:
(i) 0.5 to 99.95% by weight, based on the weight of said reaction mixture, of vinyl acetate; and
(ii) 0.05 to 25% by weight, based on the weight of said vinyl acetate, of at least one free-radical initiator; and
(2) continuously passing said reaction mixture through a heated zone wherein said reaction mixture is maintained at a temperature of at least 150° C. and a pressure of at least 30 bars for from 0.1 seconds to 4 minutes to form oligomers of vinyl acetate, wherein the reaction is conducted in a tubular reactor having no moving parts.

16. A process for forming oligomers of vinyl alcohol, comprising the steps of:
(1) forming a reaction mixture, substantially free of carboxylic-containing monomers and their salts, comprising:
(i) 0.5 to 99.95% by weight, based on the weight of said reaction mixture, of vinyl acetate; and
(ii) 0.05 to 25% by weight, based on the weight of said vinyl acetate, of at least one free-radical initiator;
(2) continuously passing said reaction mixture through a heated zone wherein said reaction mixture is maintained at a temperature of at least 150° C. and a pressure of at least 30 bars for from 0.1 seconds to 4 minutes to form oligomers of vinyl acetate, wherein the reaction is conducted in a tubular reactor having no moving parts; and
(3) hydrolyzing said oligomers of vinyl acetate in the presence of a catalyst to form oligomers of vinyl alcohol.

17. A process for forming oligomers of vinyl alcohol, comprising the steps of:
(1) forming a reaction mixture, substantially free of carboxylic-containing monomers and their salts, comprising:
(i) 0.5 to 99.95% by weight, based on the weight of said reaction mixture, of vinyl acetate; and
(ii) 0.05 to 25% by weight, based on the weight of said vinyl acetate, of at least one free-radical initiator;
(2) continuously passing said reaction mixture through a heated zone wherein said reaction mixture is maintained at a temperature of at least 150° C. and a pressure of at least 30 bars for from 0.1 seconds to 4 minutes to form oligomers of vinyl acetate, wherein the reaction is conducted in a tubular reactor having no moving parts; and
(3) transesterifying said oligomers of vinyl acetate with an alcohol in the presence of a catalyst to form oligomers of vinyl alcohol.

* * * * *